United States Patent
Nakamura et al.

(10) Patent No.: US 9,286,515 B2
(45) Date of Patent: Mar. 15, 2016

(54) DOZE DETECTION METHOD AND APPARATUS THEREOF

(75) Inventors: Kiyomi Nakamura, Toyama (JP); Hironobu Takano, Hachioji (JP)

(73) Assignee: TOYAMA PREFECTURE, Toyama-Shi, Toyama (JP)

( * ) Notice: Subject to any disclaimer, the term of this patent is extended or adjusted under 35 U.S.C. 154(b) by 32 days.

(21) Appl. No.: 14/342,720

(22) PCT Filed: Sep. 4, 2012

(86) PCT No.: PCT/JP2012/072497
§ 371 (c)(1),
(2), (4) Date: Mar. 4, 2014

(87) PCT Pub. No.: WO2013/035704
PCT Pub. Date: Mar. 14, 2013

(65) Prior Publication Data
US 2014/0205149 A1    Jul. 24, 2014

(30) Foreign Application Priority Data

Sep. 5, 2011    (JP) .................................. 2011-192591
Nov. 15, 2011   (JP) .................................. 2011-249662

(51) Int. Cl.
*G06K 9/00*    (2006.01)
*G08B 21/06*   (2006.01)
(Continued)

(52) U.S. Cl.
CPC .......... *G06K 9/00604* (2013.01); *A61B 5/1103* (2013.01); *A61B 5/18* (2013.01);
(Continued)

(58) Field of Classification Search
None
See application file for complete search history.

(56) References Cited

U.S. PATENT DOCUMENTS 5,878,156 A * 3/1999 Okumura ....................... 382/118
6,575,902 B1 * 6/2003 Burton ........................... 600/300
(Continued)

FOREIGN PATENT DOCUMENTS

EP    2 351 524 A1   8/2011
EP    2 410 501 A1   1/2012
(Continued)

OTHER PUBLICATIONS

Picot, Antoine, Alice Caplier, and Sylvie Charbonnier. "Comparison between EOG and high frame rate camera for drowsiness detection." Applications of Computer Vision (WACV), 2009 Workshop on. IEEE, 2009.*

(Continued)

*Primary Examiner* — Utpal Shah
*Assistant Examiner* — Narek Zohrabyan
(74) *Attorney, Agent, or Firm* — Holtz, Holtz & Volek PC

(57) ABSTRACT

A doze detection method, which accurately detects a blink burst and improves speed and accuracy of doze detection, includes measuring a state where the eye is substantially open as an open eye time and another state as a closed eye time, defining a time shorter than an average blink interval of a healthy adult in an alert state as a first threshold time; defining a time longer than an average closed eye time of a healthy adult in an alert state as a second threshold time; and defining blinks as a blink burst when detecting an eye opening equal to or shorter than the first threshold time. A doze state is determined when the closed eye time of a blink among the blinks during the blink burst reaches at least the second threshold time, the blink occurring after an open eye time equal to at most the first threshold time.

11 Claims, 15 Drawing Sheets

(51) Int. Cl.
*A61B 5/18* (2006.01)
*A61B 5/11* (2006.01)
*B60K 28/06* (2006.01)
*A61B 5/00* (2006.01)

(52) U.S. Cl.
CPC ............ *A61B 5/4809* (2013.01); *A61B 5/7282* (2013.01); *B60K 28/066* (2013.01); *G08B 21/06* (2013.01); *A61B 5/0077* (2013.01)

(56) References Cited

U.S. PATENT DOCUMENTS

| | | | | |
|---|---|---|---|---|
| 8,184,132 | B2* | 5/2012 | Sakamoto et al. | 345/690 |
| 8,306,271 | B2* | 11/2012 | Yoda et al. | 382/104 |
| 2009/0027212 | A1* | 1/2009 | Nakagoshi et al. | 340/575 |
| 2009/0237257 | A1* | 9/2009 | Yamada et al. | 340/575 |
| 2009/0268022 | A1* | 10/2009 | Omi | 348/135 |
| 2010/0007480 | A1* | 1/2010 | Uozumi et al. | 340/436 |
| 2011/0205350 | A1* | 8/2011 | Terashima et al. | 348/78 |
| 2011/0216181 | A1* | 9/2011 | Yoda et al. | 348/78 |
| 2011/0313259 | A1* | 12/2011 | Hatakeyama et al. | 600/300 |
| 2012/0002843 | A1* | 1/2012 | Yoda et al. | 382/103 |
| 2014/0210625 | A1* | 7/2014 | Nemat-Nasser | 340/575 |
| 2015/0137979 | A1* | 5/2015 | Nemat-Nasser | 340/575 |

FOREIGN PATENT DOCUMENTS

| | | |
|---|---|---|
| JP | 2006-136556 A | 6/2006 |
| JP | 2008065776 A | 3/2008 |
| JP | 2008-073335 A | 4/2008 |
| JP | 2010-068848 A | 4/2010 |
| JP | 2010-224637 A | 10/2010 |
| WO | WO 2010/032725 A1 | 3/2010 |
| WO | WO 2010/107066 A1 | 9/2010 |

OTHER PUBLICATIONS

Bharambe, Ms Snehal S., and P. M. Mahajan. "Driver Drowsiness Detection: A Review." International Journal of Infinite Innovations in Technology vol. III, Issue II , 2014-2015.*

Picot, Antoine, Sylvie Charbonnier, and Alice Caplier. "Drowsiness detection based on visual signs: blinking analysis based on high frame rate video."Instrumentation and Measurement Technology Conference (I2MTC), 2010 IEEE. IEEE, 2010.*

Caffier, Philipp P., Udo Erdmann, and Peter Ullsperger. "Experimental evaluation of eye-blink parameters as a drowsiness measure." European journal of applied physiology 89.3-4 (2003): 319-325.*

Tabrizi, Pooneh R., and Reza A. Zoroofi. "Open/closed eye analysis for drowsiness detection." Image Processing Theory, Tools and Applications, 2008. IPTA 2008. First Workshops on. IEEE, 2008.*

Collected Papers B-3 of 2010 Joint Conference of Hokuriku Chapters of Electrical Societies (Heisei 22 nendo denki kankei gakkai hokurikushibu rengou taikai kouen ronbunshuu B-3).

Collected Papers (pp. 25 and 26) of 2010 Conference of Hokuriku Chapters of Japanese Society for Medical and Biological Engineering (Heisei 22 nendo nihon seitaiikougakkai hokurikusibutaikai kouen 15, ronbunshuu pp. 25 to 26).

International Search Report (ISR) dated Dec. 18, 2012 (and English translation thereof) issued in International Application No. PCT/JP2012/072497.

International Preliminary Report on Patentability (IPRP) including Written Opinion dated Mar. 12, 2014 in parent International Application No. PCT/JP2012/072497.

Extended European Search Report (EESR) dated Apr. 9, 2015 issued in counterpart European Application No. 12829487.3.

* cited by examiner (a) Blink interval is defined as the period of open eye.

(b) Blink interval is defined as the period between bottoms of area of iris.

Fig. 9
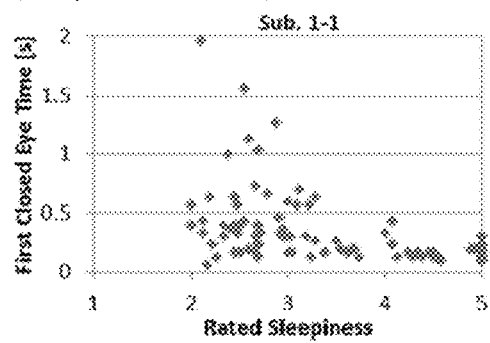
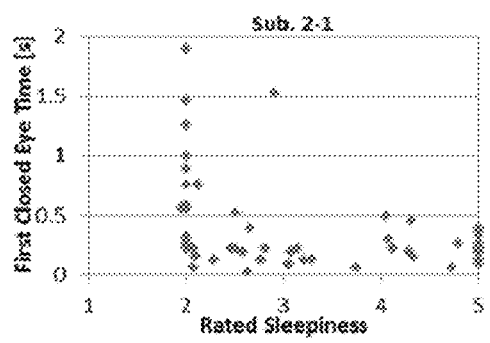
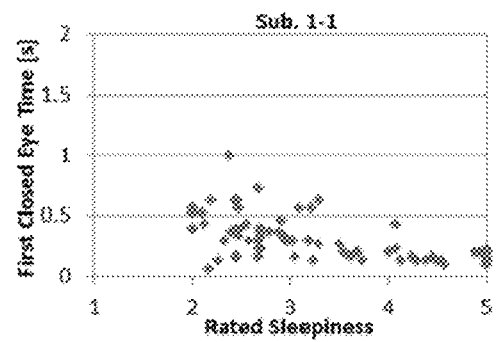
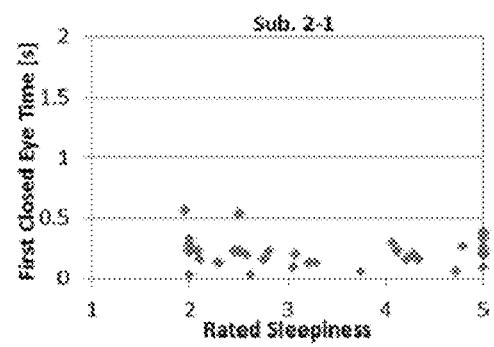

Fig. 10
[Proposed Method]
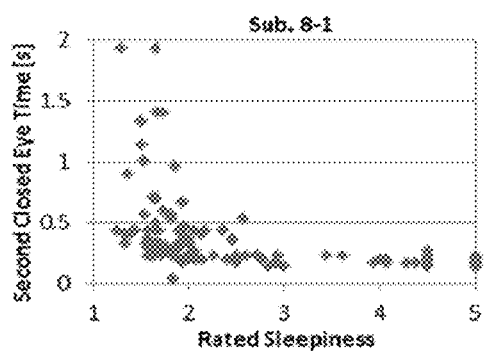
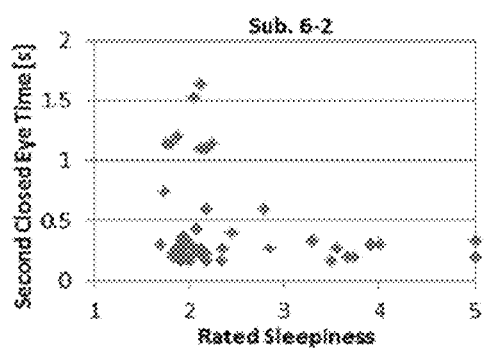
[Previous Method]
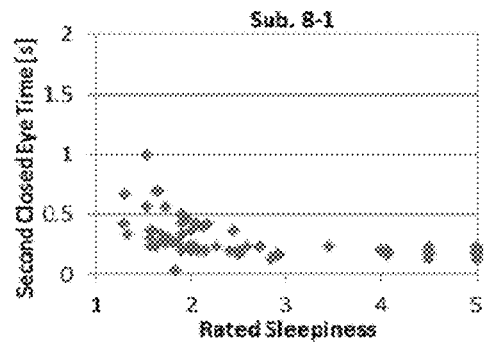
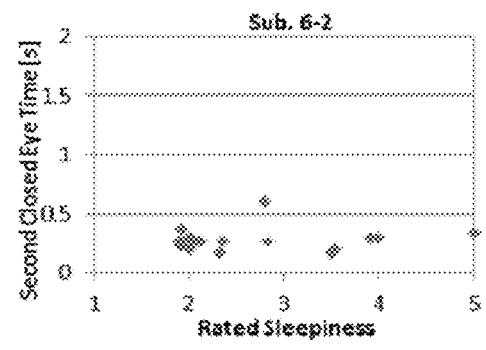

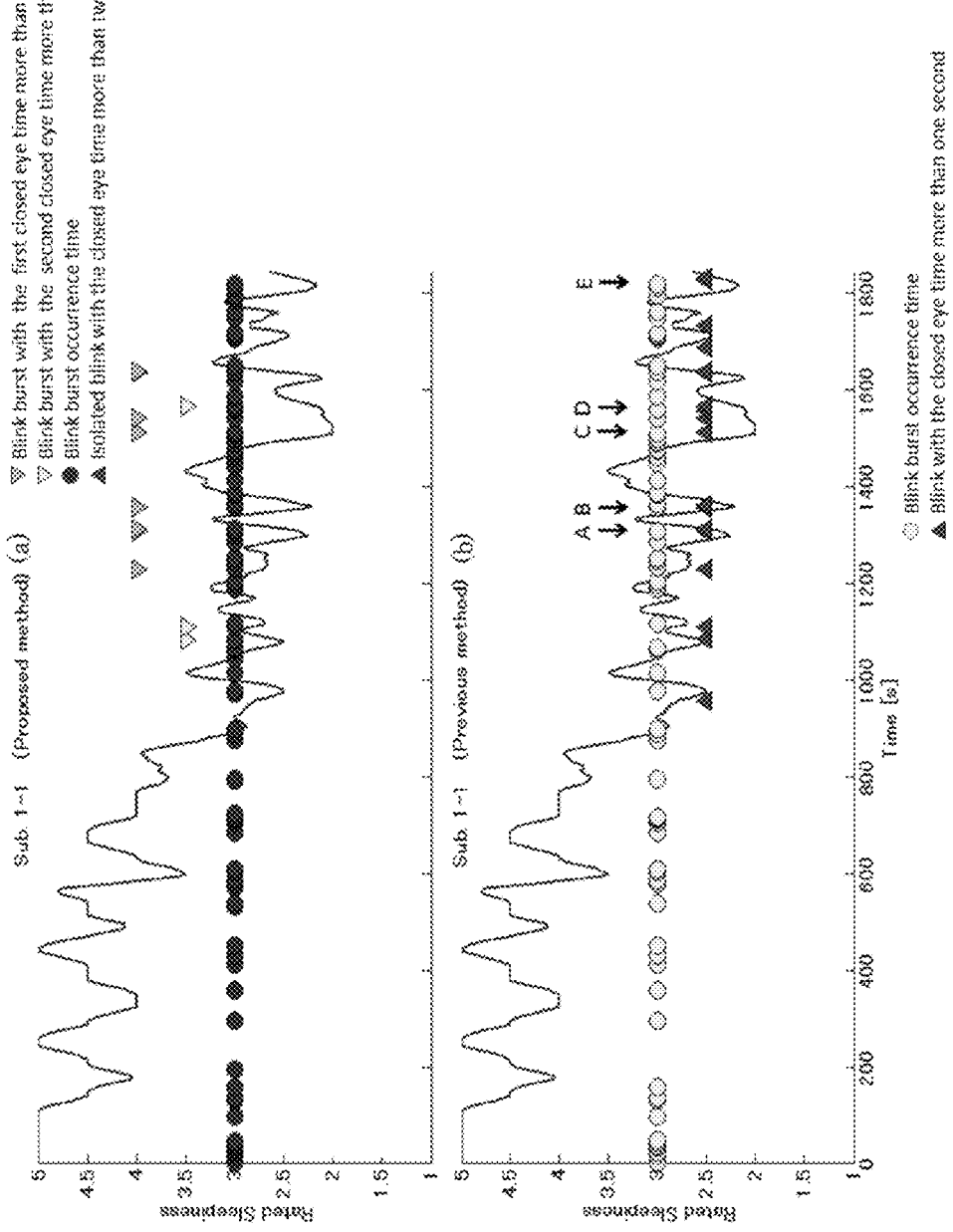

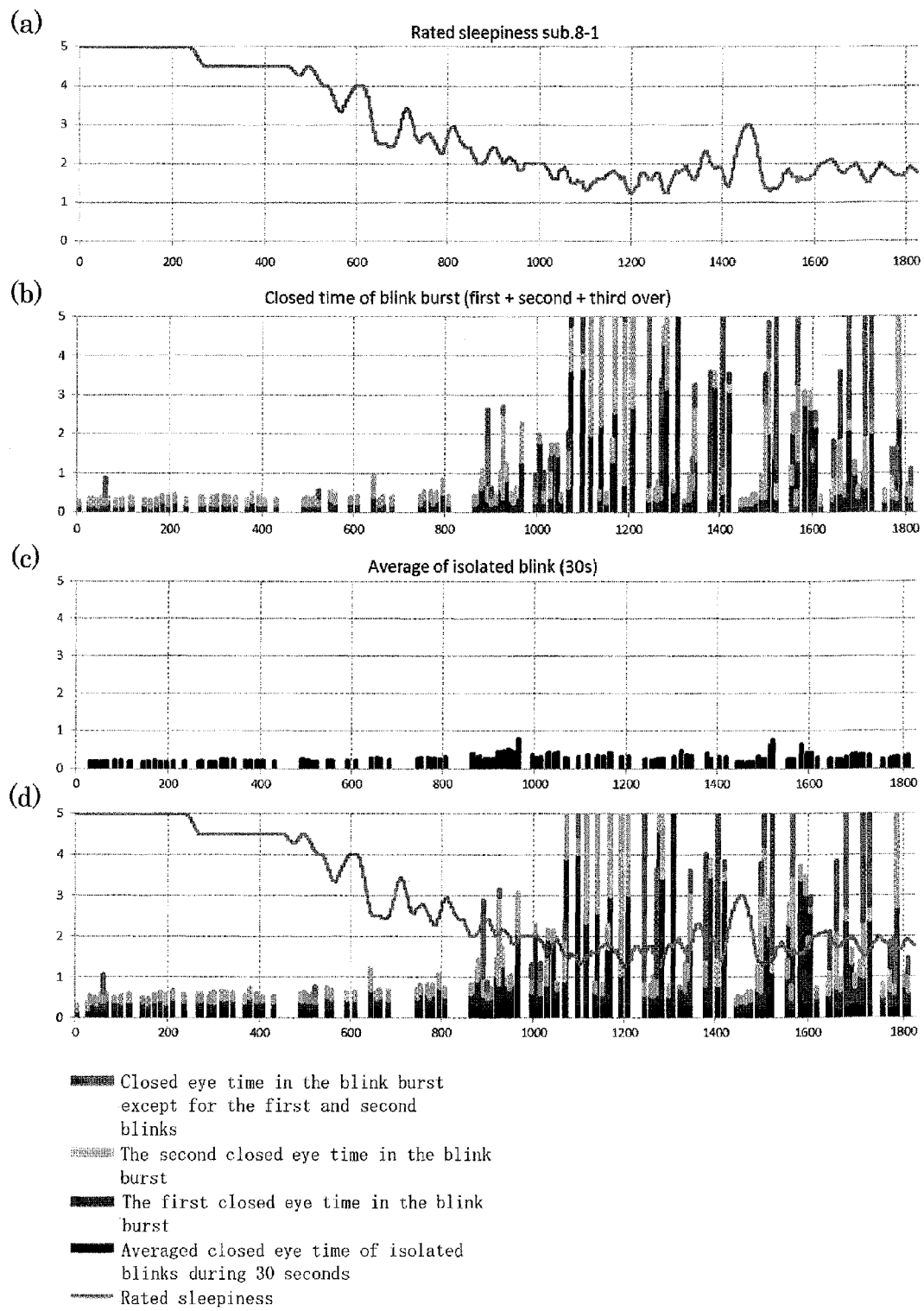

DOZE DETECTION METHOD AND APPARATUS THEREOF

TECHNICAL FIELD

The present invention relates to a doze detection method of detecting a doze, which means a state where an arousal level of a human is lowered, and relates also to an apparatus thereof.

BACKGROUND ART

As a method of detecting a doze, conventionally, a method is proposed in which a decrease in an arousal level is detected by detecting a blink burst, which means a state where a plurality of eye closures occur in a short time, for example, within 1 second. For example, Patent Literature 1 discloses a detection method in which it is determined that the arousal degree decreases (it is in a doze state) when a slow eye movement (SEM) which is a lateral movement of an eyeball accompanying closing of the eyelids is detected within a predetermined time from detecting a burst of blink. The burst of blink and SEM are characteristic phenomena appearing in the early stage of sleep onset, and a decrease in arousal degree is determined by the combination thereof.

Patent Literature 2 discloses an arousal decrease detection apparatus that includes a blink detection means that detects a blink of a subject, a blink determination means that determines, among the blinks detected by the blink detection means, a blink in a blink burst in which a blink interval between the blink and the immediately-preceding blink is within a predetermined time and a blink with a long eye-closure for a predetermined time or longer, and an arousal decrease determination means that determines an arousal decrease degree on the basis of a time from the blink of the blink burst to the blink with the long eye-closure.

However, blinks are extracted without distinguishing between normal blinks and a blink burst in the detection method described in Patent Literature 2, and thus, the extraction method is not specialized for a blink burst. Accordingly, in the detection method described in Patent Literature 2, a blink phenomenon, often observed during a blink burst, in which an eye transitions from closed to half-open and then back to closed, cannot be detected, so that there is a problem that blink bursts cannot be detected with high accuracy.

Therefore, in order to detect a blink burst with high accuracy, Patent Literature 3 proposes that a drowsiness assessment device which includes an image capture means that successively captures an image of a region including an eye of an assessment subject, an openness detection means that detects time series data of eyelid openness on the basis of the images successively captured by the image capture means, a blink burst detection means that on the basis of the eyelid openness time series data detected by the openness detection means extracts any maximum values and minimum values from a range in which the eyelid openness is continuously less than a predetermined threshold value and detects blink bursts when a blink interval detected at a threshold value set between an extracted maximum value and an extracted minimum value is within a predetermined time, and a drowsiness state assessment means that assesses the state of sleepiness of the assessment subject on the basis of the result detected by the blink burst detection means.

On the other hand, in Non Patent Literatures 1 and 2, a relation between a closed eye time of the first blink during a blink burst and rated sleepiness is investigated in order to detect a doze state only on the basis of a characteristic of a blink. It is described that, as a result, when an arousal degree decreases, the closed eye time of the first blink becomes longer.

CITATION LIST

Patent Literature

[PTL 1] Japanese Unexamined Patent Application Publication No. 2006-136556
[PTL 2] Japanese Unexamined Patent Application Publication No. 2008-73335
[PTL 3] Japanese Unexamined Patent Application Publication No. 2010-224637

Non Patent Literature

[NPL 1] Collected Papers B-3 of 2010 Joint Conference of Hokuriku Chapters of Electrical Societies (Heisei 22 nendo denki kankei gakkai hokurikushibu rengou taikai kouen ronbunshuu B-3)
[NPL 2] Collected Papers pp. 25 to 26 of 2010 Conference of Hokuriku Chapters of Japanese Society for Medical and Biological Engineering (Heisei 22 nendo nihon seitaiikougakkai hokurikusibutaikai kouen ronbunshuu pp. 25 to 26)

SUMMARY OF INVENTION

Technical Problem

As shown in FIG. 2(b) and FIG. 3(b), in the detection of a blink bust according to the inventions disclosed in the Patent Literatures 1 and 2 of the above-described background arts, a time between a minimum value of eye closure and a next minimum value of eye closure is generally measured as a blink interval $TO_p(i)$. Further, a determination reference value $Th_O$ is set to i.e. 1 second, and a case when the blink interval $TO_p(i)$ is not more than the determination reference value $Th_O$ is defined as a blink burst. In the blink interval $TO_p(i)$ in this case, a time between the minimum value of the closed eye state and eye opening, and a time between the open eye state and an extreme value of eye closure are included in the measurement, and blinks during a blink burst in which a time for the action of closing or opening an eyelid becomes long cannot be detected. Therefore, it is not possible to accurately detect a blink burst.

In the detection method disclosed in Patent Literature 3, time series data of eyelid openness is detected, and on the basis of the detected eyelid openness time series data, it is determined to be a blink burst within a range in which the eyelid openness is continuously less than a predetermined threshold value, and thus, it is difficult to accurately measure the eyelid openness in a half closed state, and a measurement error is likely to occur.

In Non Patent Literatures 1 and 2, a reference for detecting a doze state from the closed eye time of a blink during blink burst and real time detection timing are not mentioned, and thus, it is not possible to accurately determine a doze state. Further, in the determination of a doze state based only on the closed eye time of the first blink during a blink burst, the doze detection accuracy is low, and there is a problem that the doze detection timing delays.

The present invention has been achieved in view of the aforementioned problem of the background art, and an object of the present invention is to provide a doze detection method, using a relatively simple apparatus, with which it is possible to accurately detect a blink burst and to improve the speed and the accuracy of detecting a doze state, and provide also an apparatus thereof.

Solution to Problem

The present invention is a doze detection method that includes: measuring, among states from an eye closure to an eye opening of a human eye, a state where the eye is substantially open as an open eye time and the other state as a closed eye time; defining a time that is relatively shorter than an average blink interval of healthy adult in an alert state as a first threshold time (determination reference value $Th_O$ of blink burst); defining a time that is relatively longer than an average closed eye time of healthy adult in an alert state as a second threshold time (doze determination reference $Th_{C1}$); when detecting an eye opening equal to or shorter than the first threshold time (s2), defining blinks before and after the eye opening as a blink burst; and determining to be a doze state when a closed eye time of a blink among the blinks during the blink burst reaches the second threshold time or more (s5), the blink occurring after an open eye time equal to or shorter than the first threshold time.

Further, the present invention is the doze detection method, in which it is immediately determined to be a doze state when a closed eye time of a blink among the blinks during the blink burst is equal to or longer than the second threshold time (s3), the blink occurring before an open eye time equal to or shorter than the first threshold time.

The present invention is the doze detection method, in which a closed eye time that is relatively longer than the second threshold time is defined as a third threshold time, and it is immediately determined to be a doze state when a closed eye time of a blink among the blinks during the blink burst reaches the third threshold time (doze determination reference $Th_{C2}$) or more (s6), the blink occurring after an open eye time equal to or shorter than the first threshold time.

The present invention is the doze detection method, in which a closed eye time that is relatively longer than the second threshold time is defined as a third threshold time, in detecting the open eye time, when detecting an eye opening longer than the first threshold time and when an open eye time before a blink immediately preceding the eye opening occurs is longer than the first threshold time, the immediately-preceding blink is determined to be a blink other than a blink burst, and it is immediately determined to be a doze state when a closed eye time of the blink other than a blink burst is equal to or longer than the third threshold time (s9).

The present invention is the doze detection method, in which a closed eye time that is relatively longer than the second threshold time is defined as a third threshold time, and in detecting the open eye time, when detecting an eye opening longer than the first threshold time and when a closed eye time of a blink immediately after the eye opening reaches the third threshold time or more (s11), it is immediately determined to be a doze state. For example, the third threshold time may be a closed eye time relatively longer than an average closed eye time of blinks other than the blink burst of healthy adult in an alert state.

In addition, it may be determined to be a doze state, when a total closed eye time obtained as a sum of the closed eye time of the blink during the blink burst and the closed eye time of the blink other than the blink burst is relatively longer than the third threshold time, for example. Further, the total closed eye time may be obtained by weighting the closed eye time of the blink during the blink burst and the closed eye time of the blink other than the blink burst respectively, and by adding the weighted closed eye times.

Further, the present invention is a doze detection apparatus that includes: an eye closure detection means that detects states from an eye closure to an eye opening of the eye by recognizing a position of a human eye; and a blink time measurement means that measures a state where the human eye is substantially open as an open eye time and the other state as a closed eye time by the eye closure detection means, wherein the doze detection apparatus: defines a time that is relatively shorter than an average blink interval of healthy adult in an alert state as a first threshold time (determination reference value $Th_O$ of blink burst); defines a time that is relatively longer than an average closed eye time of healthy adult in an alert state as a second threshold time (doze determination reference $Th_{C1}$); and when detecting an eye opening equal to or shorter than the first threshold time, defines blinks before and after the eye opening as a blink burst, and the doze detection apparatus further includes: a blink burst discrimination means that discriminates the blink burst on the basis of a time of the blink measured by the blink time measurement means; and a doze discrimination means that determines to be a doze state when the blink burst is detected, and when a closed eye time of a blink, among the blinks during the blink burst, occurring after an open eye time equal to or shorter than the first threshold time reaches the second threshold time or more.

Further, the doze detection apparatus includes the doze discrimination means that immediately determines to be a doze state when a closed eye time of a blink among the blinks during the blink burst is equal to or longer than the second threshold time, the blink occurring before an open eye time equal to or shorter than the first threshold time.

The present invention is the doze detection apparatus, in which a closed eye time that is relatively longer than the second threshold time is defined as a third threshold time, and the doze discrimination means immediately determines to be a doze state when a closed eye time of a blink among the blinks during the blink burst detected by the blink burst discrimination means reaches the third threshold time (doze determination reference $Th_{C2}$) or more, the blink occurring after an open eye time equal to or shorter than the first threshold time.

The present invention is the doze detection apparatus, in which a closed eye time that is relatively longer than the second threshold time is defined as a third threshold time, and when detecting an eye opening longer than the first threshold time by the blink time measurement means and when an open eye time before a blink immediately preceding the eye opening occurs is longer than the first threshold time, the immediately-preceding blink is determined to be a blink other than a blink burst, and the doze discrimination means immediately determines to be a doze state when a closed eye time of the blink other than a blink burst is equal to or longer than the third threshold time.

The present invention is the doze detection apparatus, in which a closed eye time that is relatively longer than the second threshold time is defined as a third threshold time, and when detecting an eye opening longer than the first threshold time by the blink time measurement means and when a closed eye time of a blink immediately after the eye opening reaches the third threshold time or more, the doze discrimination means immediately determines to be a doze state. For example, the third threshold time may be a closed eye time relatively longer than an average closed eye time of blinks other than the blink burst of healthy adult in an alert state.

The doze discrimination means determines to be a doze state, when a total closed eye time obtained as a sum of the closed eye time of the blink during the blink burst detected by the blink burst discrimination means and the closed eye time of the blink other than the blink burst that is detected by the blink time measurement means is relatively longer than the third threshold time, for example. The doze discrimination means also obtains the total closed eye time by weighting the closed eye time of the blink during the blink burst and the closed eye time of the blink other than the blink burst respectively, and by adding the weighted closed eye times.

The present invention may be the doze detection apparatus, including an alert means issuing a doze alert on the basis of the determination result of a doze state.

Furthermore, the present invention can be applied to a vehicle comprising the doze detection apparatus.

Advantageous Effects of Invention

The doze detection method and apparatus thereof of the present invention use a simple device, do not incur a high cost, and can detect a doze accurately and rapidly. Therefore, a doze of a driver in a vehicle, for example, can be found quickly and it is possible to enhance driving safety.

BRIEF DESCRIPTION OF DRAWINGS

FIG. 9 shows a distribution of first closed eye times according to a definition of a blink burst in the present invention, and a distribution of first closed eye times according to a conventional definition of a blink burst, for two subjects.

FIG. 10 shows a distribution of second closed eye times according to the definition of a blink burst in the present invention, and a distribution of second closed eye times according to the conventional definition of a blink burst, for two subjects.

FIG. 16 is a graph (a) showing doze detection according to an example of the present invention, and a graph (b) showing doze detection according to the conventional art.

FIG. 17 is a graph (a) showing rated sleepiness, a graph (b) showing a total closed eye time of blinks during a blink burst, a graph (c) showing an average closed eye time of isolated blinks, and a graph (d) showing the sum of the total closed eye time of blinks in a blink burst and the isolated blink, according to an example of the present invention.

DESCRIPTION OF EMBODIMENTS

Figure 1:
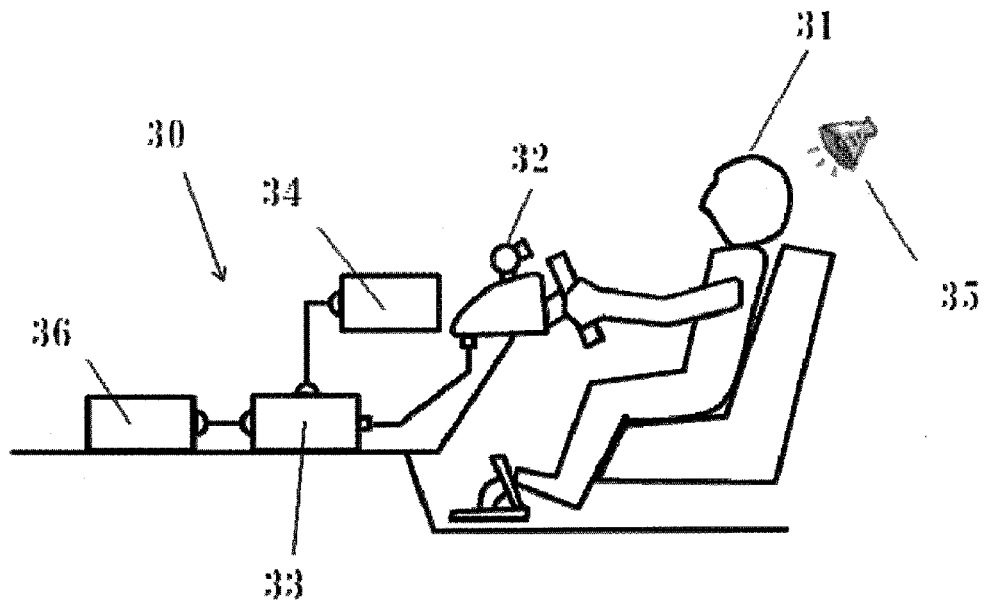
FIG. 1 is a schematic view of a doze detection apparatus according to an embodiment of the present invention.

Hereafter, a description of an embodiment of the present invention will be given on the basis of the drawings. FIG. 1 to FIG. 7 show an embodiment of the present invention. As shown in FIG. 1, a doze detection apparatus 30 of the present embodiment includes a photographing unit 32, including a CCD camera and the like, that photographs a face of a driver 31, and a driver monitor ECU 33 in which a doze detection algorithm performing detection and the like of a blink by processing an image generated by the photographing unit 32 is implemented, for example. The driver monitor ECU 33 is connected to a navigation system 34 displaying an arousal level and visually calling an alert when a doze state occurs. Further, the driver monitor ECU 33 calls an alert also by sound by a speaker 35 when the driver 31 enters a doze state. Furthermore, the driver monitor ECU 33 performs brake control of a vehicle by a brake control device 36, when the doze state of the driver 31 continues.

The driver monitor ECU 33 includes a CPU, a ROM that stores a program such as a control routine, a RAM that stores data and the like, and a storage device, that stores other program or data, such as a hard disk.

A doze detection function provided in the driver monitor ECU 33 is configured by an execution program of the doze detection algorithm that includes an eye closure detection means that detects a blink defined in the present invention by processing an image photographed by the photographing unit 32, a blink time measurement means that measures an open eye time and a closed eye time of the blink detected by the eye closure detection means, a blink burst discrimination means that discriminates a blink burst on the basis of the time of blink measured by the blink time measurement means, and a doze discrimination means that determines a doze on the basis of these measurement results.

Figure 3:
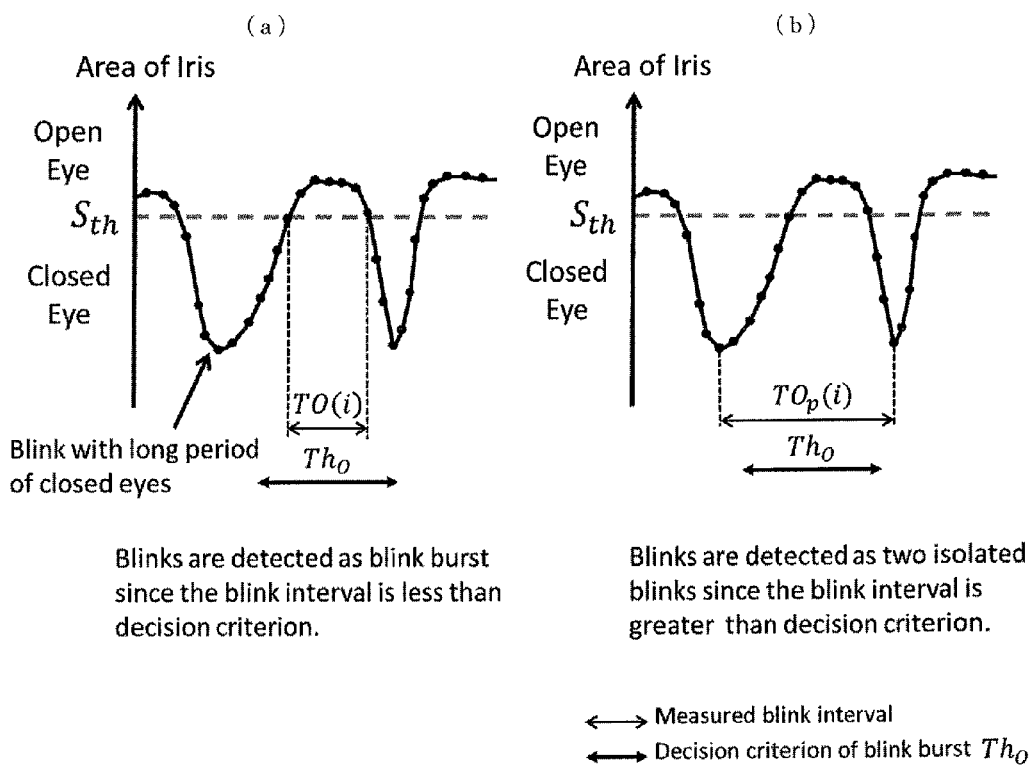
FIG. 3 is a time chart showing a detection (a) of a blink according to the doze detection method of an embodiment of the present invention, and a conventional detection (b) of a blink, when a closed eye time is long.
Figure 4:
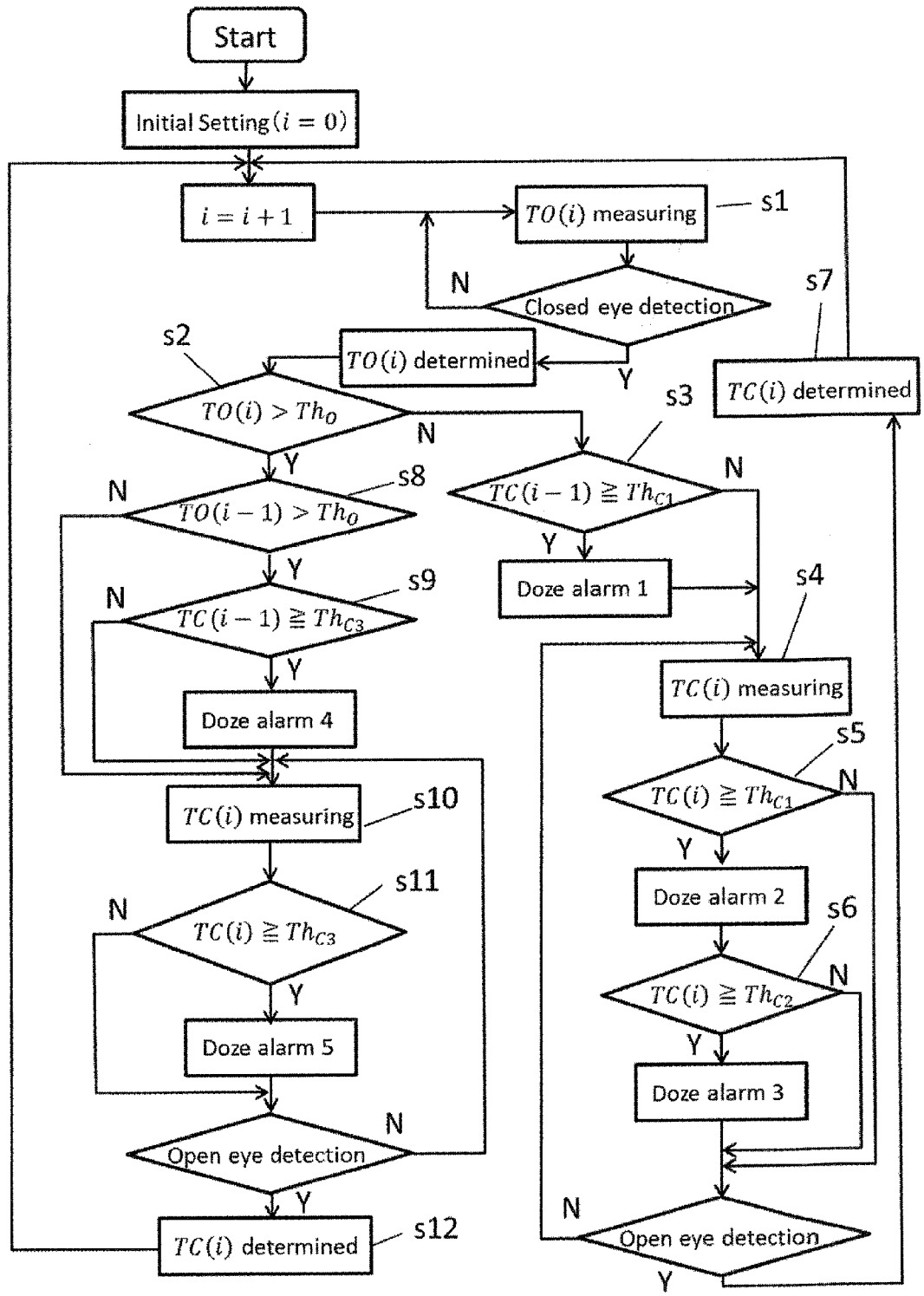
FIG. 4 is a flowchart showing the doze detection method according to an embodiment of the present invention.

The detection and determination of a doze state are performed on the basis of determination of a blink burst based on an open eye time TO(i) shown in FIG. 2(a) and FIG. 3(a), as shown in a flowchart of FIG. 4. Firstly, the open eye time TO(i) (i is a natural number) is measured by the blink burst discrimination means provided in the driver monitor ECU 33 (s1). It is checked whether the open eye time TO(i), which is finalized by detecting a closed eye state by the eye closure detection means during the measurement, is equal to or shorter than the determination reference value $Th_O$ shown in FIG. 3(a), which is a first threshold time (s2). When the open eye time TO(i) is equal to or shorter than the determination reference value $Th_O$ of blink burst, a blink that occurred before the open eye state and a blink that will occur after the open eye state are determined as a blink burst. In this embodiment, the determination reference value $Th_O$=1 second. At this time, when a closed eye time TC(i–1) of the blink that occurred before the open eye state is equal to or longer than a doze determination reference $Th_{C1}$ which is a second threshold time, the doze discrimination means determines to be a doze state at that time point (s3, early doze determination step), and then, a doze alert 1 is issued by, for example, sound. Here, among states from an eye closure to an eye opening of a human eye, a state where the eye is substantially open is defined as an open eye time and the other state is defined as a closed eye time. Further, a time that is relatively shorter than an average open eye time of a healthy adult in an alert state is defined as the first threshold time (determination reference value $Th_O$ of blink burst based on open eye time). Furthermore, a time that is relatively longer than an average closed eye time of a healthy adult in an alert state is defined as the second threshold time (doze determination reference $Th_{C1}$).

Next, a closed eye time TC(i) is measured by the blink burst discrimination means (s4). When the closed eye time TC(i) becomes equal to or longer than the doze determination reference $Th_{C1}$, it is immediately determined to be a doze state (s5, first doze determination step), and a doze alert 2 is issued by, for example, sound. Further, when the closed eye time TC(i) becomes equal to or longer than another doze determination reference $Th_{C2}$ (doze determination reference $Th_{C2}$>doze determination reference $Th_{C1}$) which is a third threshold time longer than the second threshold time, it is determined to be a doze state again (s6, second doze determination step) and a doze alert 3 is issued by, for example, sound. Then, when an open eye state is detected by the eye closure detection means, it is determined that the blink ends, and the closed eye time TC(i) is finalized by the blink burst discrimination means (s7). Here, although the third threshold time is set to a closed eye time that is relatively longer than the second threshold time, if necessary, for example, the third threshold time may be a closed eye time relatively longer than a total time of an average closed eye time of blinks occurring before the eye opening equal to or shorter than the first threshold time and an average closed eye time of blinks occurring after the eye opening equal to or shorter than the first threshold time, or may be a closed eye time relatively longer than an average closed eye time of blinks other than the blink burst of a healthy adult in an alert state.

On the other hand, when the open eye time TO(i) is longer than the determination reference value $Th_O$ of blink burst, and when the open eye time TO(i–1) before a blink immediately preceding the open eye state is longer than the determination reference value $Th_O$ of blink burst, the blink immediately preceding the open eye state is determined to be an isolated blink (a blink other than a blink burst, s8). Further, when the closed eye time TC(i–1) of the blink immediately preceding the open eye state is equal to or longer than the another doze determination reference $Th_{C3}$, which is defined as a fourth threshold time that is another value longer than the second threshold time (doze determination reference $Th_{C3}$>doze determination reference $Th_{C1}$), it is determined to be a doze state (s9), and then, a doze alert 4 is issued by, for example, sound. Next, the closed eye time TC(i) is measured by the blink burst discrimination means (s10). When the closed eye time TC(i) becomes equal to or longer than the doze determination reference $Th_{C3}$, it is immediately determined to be a doze state (s11), and a doze alert 5 is issued by, for example, sound. Then, when an open eye state is detected by the eye closure detection means, it is determined that the blink ends, and the closed eye time TC(i) is finalized by the blink burst discrimination means (s12). Here, although the fourth threshold time is set to a closed eye time that is relatively longer than the second threshold time, if necessary, for example, the fourth threshold time may be a closed eye time relatively longer than an average closed eye time of isolated blinks (blinks other than the blink burst) of a healthy adult in an alert state.

Figure 5:
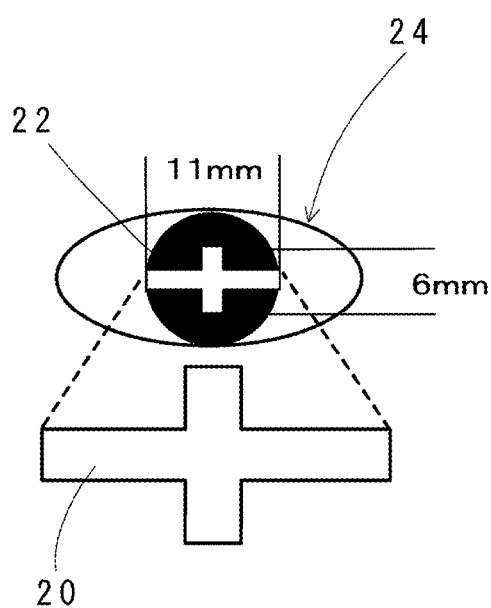
FIG. 5 is a schematic view of a template used in an eye detection method of the doze detection apparatus according to an embodiment of the present invention.

Hereinafter, an example of a blink detection method will be described. Firstly, in an eye position detection method, a gray image of a face acquired by the photographing unit 32 is binarized by threshold value processing, template matching by a one eye portion template 20 shown in FIG. 5 is performed on the binarized image. For example, a sequential similarity detection method is used for the template matching.

Generally, as shown in FIG. 5, the diameter of a cornea of an adult's eye 24 is about 11 mm (9.3 to 11 mm in vertical width, 10.6 to 12 mm in horizontal width). The size of an iris 22 which is a pupil substantially matches the size of the cornea, and thus, the size of the iris 22 is set to 11 mm in diameter in the embodiment. The one eye portion template 20 is configured by straight lines forming a cross, and is set to 11 mm in horizontal width and 6 mm in vertical width on the screen of a monitor 16, for example. A line having a certain length is drawn on the monitor 16, and the number of pixels per 1 mm is calculated on the basis of the number of pixels of the line. In this embodiment, 1 mm corresponds to 4.2 pixels, 11 mm corresponds to about 46 pixels, and 6 mm corresponds to about 25 pixels. By using such cross shaped one eye portion template 20, even when the eye 24 is inclined, the circular iris 22 is not affected, and thus, it is possible to achieve accurate matching with the iris 22.

In this embodiment, in order to accelerate the processing, for example, the template matching is performed while moving the one eye portion template 20 by four pixels. A matching degree of the one eye portion template 20 in horizontal width is compared for every pixel in the image, and a matching degree of the one eye portion template 20 in vertical width is compared for every other pixel. When the matching degrees in horizontal width of 90% or more and matching degree in vertical width of 40% or more are both satisfied, it is determined that a portion with which the one eye portion template 20 overlaps is assumed as an eye.

Figure 6:
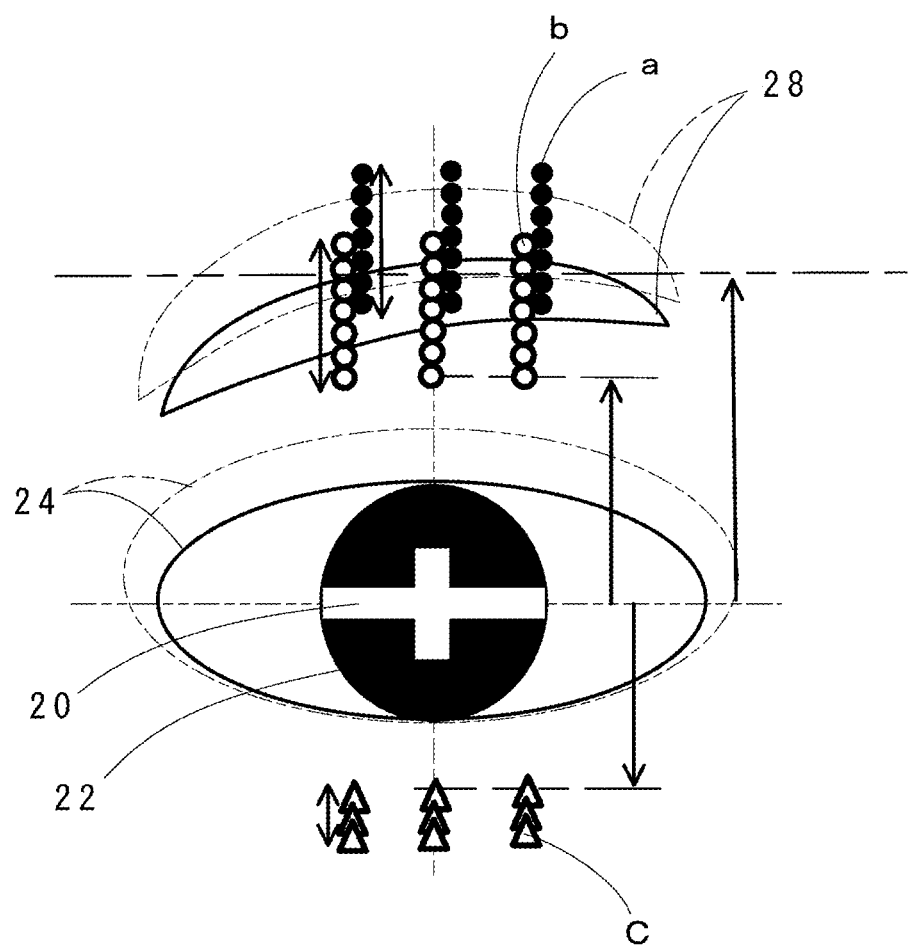
FIG. 6 is a view showing a principle of the eye detection method of the doze detection apparatus according to an embodiment of the present invention.

Any eye-like portions on the image may be detected by the template matching using the one eye portion template 20 in error. As a countermeasure against the error, characteristics around the eye 24 are used as check items, i.e. as shown in FIG. 6, the existence of an eyebrow 28 on the upper and lower portions of the one eye portion template 20 is used as information for making a decision. For example, when the iris 22 has a size of 11 mm, while individual differences of human faces are taken into consideration, a checkpoint a of a position of the eyebrow 28 is set from 25 to 50 mm above from the center of the one eye portion template 20, a checkpoint b between the eyebrow 28 and eye 24 is set from 15 to 27 mm above from the center, a checkpoint c below the eye 24 is set from 15 to 22 mm from the center, and each binarized value of the pixel is compared with a threshold value to be determined. As a result, from the binarized image data, it is possible to handle the following matters as information for making a decision whether an eye is detected. That is, there is no black portion immediately above the eye 24, a black portion that is the eyebrow 28 is detected above thereof, and there is no black portion below the eye 24.

Compared with a threshold value based on a value of pixel, when, at the portion above the eye 24, a matching degree of 10% or more at the position of the eyebrow 28 and a matching degree of 20% or more at the position between the eyebrow 28 and the eye 24, and, a matching degree of 20% or more at the position below the eye 24 are obtained, it is determined that the matching degrees of these check items satisfy a conditional matching of a periphery of the eye 24. In addition, a final determination to determine to be the eye 24 is made by the template matching using the one eye portion template 20 and characteristic check items around the eye 24.

Figure 2:
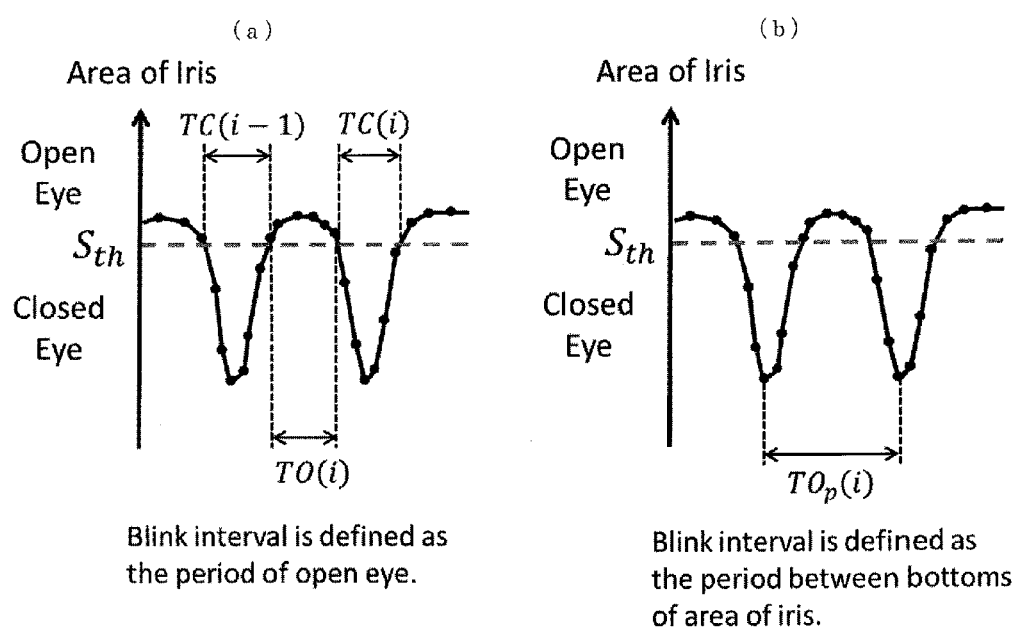
FIG. 2 is a time chart showing a definition (a) of a blink according to a doze detection method of an embodiment of the present invention, and a conventional definition (b) of a blink.

After detecting the eye 24, a blink of the eye 24 is detected. In the blink detection, a blink is detected on the basis of variation of the area of the iris 22 which is a dark portion, as shown in FIG. 2(*a*) and FIG. 3(*a*). In the blink detection, the area of the iris 22 is measured from a gray image acquired by a photographing unit 12. For example, the maximum value of the area of the iris 22 is stored and an area narrower than the maximum value by 5% to 15%, preferably by 10% is set as a threshold value $S_{th}$, and an open eye state is determined by whether the measurement result of area of the iris 22 is equal to or greater than the predetermined threshold value $S_{th}$.

Figure 7:
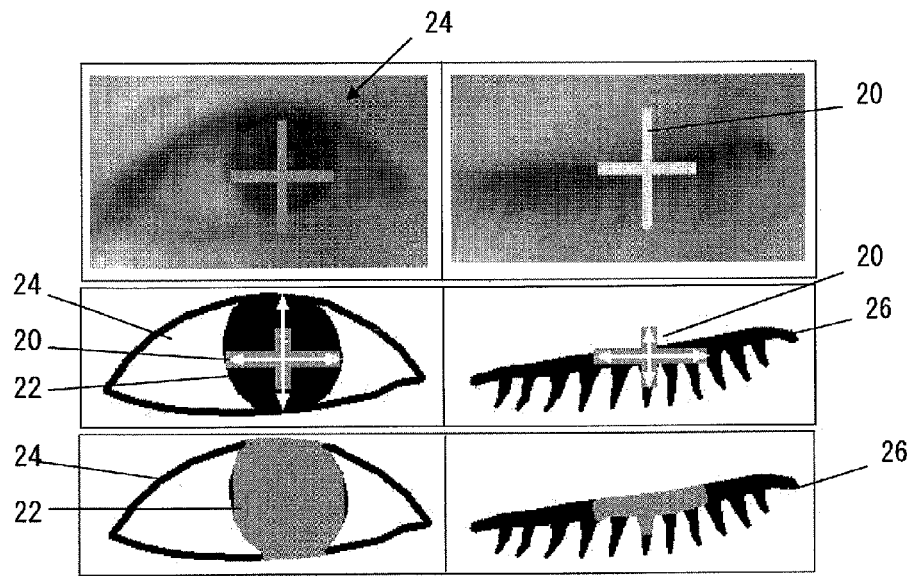
FIG. 7 is a picture and a schematic view showing a blink detection method of the doze detection apparatus according to an embodiment of the present invention.

The area of the iris 22 is measured by scanning the binarized image of the eye 24. Firstly, when a matching degree in horizontal width between the iris 22 and the one eye portion template 20 is, for example, 85% to 95%, preferably 90% or more, it is determined to be possibly an eye, and it is determined that the horizontal width of the iris 22 when the eye is open matches with the horizontal width of the one eye portion template 20. Further, as shown in FIG. 7, when the eye is closed, a black portion long in a horizontal direction is generated by eyelashes 26. Thus, in order not to overmeasure the true area, a measurement range of the area of iris 22 in the horizontal direction is set to the horizontal width of the one eye portion template 20. Furthermore, there are several points matching the one eye portion template 20 in the iris 22, and thus, while deviation of the match point from the center of the iris 22 is taken into consideration, the measurement range in the vertical direction is set a range within 50 pixels in a vertical direction from the center of the one eye portion template 20, for example.

In a procedure of measuring the iris area, the area of iris 22 is measured after the recognition of the eye 24. A movement to the left from the center position of the one eye portion template 20 is performed until a pixel density value becomes equal to or more than a binarized threshold value of the iris 22, and the resultant movement distance is calculated. Next, in a similar way, a distance in the right direction is also calculated, and the sum of the movement distances in the right and left direction is set to the horizontal width of the iris 22. Further, the horizontal widths are summed by repeating the similar work within the measurement range and above the one eye portion template 20. Furthermore, in the similar way, the horizontal widths are summed below the one eye portion template 20. This measurement is performed in the similar way when the eye is closed. When the eye is closed, a black portion long in a horizontal direction that is generated by the eyelashes 26 appears. However, the measurement range in the horizontal direction is the horizontal width of the one eye portion template 20, and a black portion with low pixel density equal to or lower than the binarized threshold value of the iris 22 becomes the vertical width of the eyelashes 26 in the vertical direction. Accordingly, within the measurement range, the area of the iris 22 when the eye is open has a value larger than a value in a case where the eyelashes 26 is measured when the eye is closed.

As a result, when the sum of black points (portions within the movement distance) with low pixel density value equal to or lower than the binarized threshold value of the iris 22 within the measurement range in FIG. 7 is equal to or more than the predetermined threshold value $S_{th}$ shown in FIG. 2 and FIG. 3, it is determined to be the iris 22 and also determined that the eye is in an open state. Further, when the sum is equal to or less than the threshold value $S_{th}$, it is determined that the eye is in a closed state.

In a method of using the doze detection apparatus 30 of the present embodiment, the doze detection apparatus 30 is provided near a driver's seat of an automobile, a train, or another working machine, a driver is photographed by the photographing unit 32, a blink burst is detected by processing based on the above-described first threshold time (determination reference value $Th_O$), when any one of closed eye times of blinks during the blink burst is equal to or longer than the second threshold time (doze determination reference $Th_{C1}$), it is determined to be a doze state, further, when a closed eye time of a blink other than the blink burst is equal to or longer than the fourth threshold time (doze determination reference $Th_{C3}$), it is also determined to be a doze state. Then, the doze alerts 1-5 can be issued by, for example, sound, and other controls may be performed. Thus, it is possible to drastically enhance driving safety of an automobile and the like.

In the above-described general blink burst detection method, as shown in FIG. 2(*b*) and FIG. 3(*b*), a time between minimum values of eye closures is measured as the blink interval $TO_p(i)$. However, there are atypical methods in which a time between a start of an eye closure and a start of a next eye closure is measured as a blink interval $TO_p(i)$, or in which a time between an end of an eye closure and an end of a next eye closure is measured as a blink interval $TO_p(i)$. However, these atypical measurement methods cannot detect blinks during a blink burst including long eye-closures, and thus, these atypical methods do not resolve the problem of the above-described general blink burst detection method. Accordingly, it can be said that the blink burst detection method according to the present invention is better in doze detection.

In the doze detection apparatus of the present embodiment, a blink burst is detected by the first threshold time (determination reference value $Th_O$) only on the basis of an open eye time as a determination reference, a closed eye time of each blink during a blink burst is determined by the second threshold time (doze determination reference $Th_{C1}$), and a closed eye time of a blink other than the blink burst is determined by the fourth threshold time (doze determination reference $Th_{C3}$), thereby rapidly discriminating a doze state. Thus, the doze detection apparatus contributes to securely prevent a doze.

EXAMPLES

Figure 8:
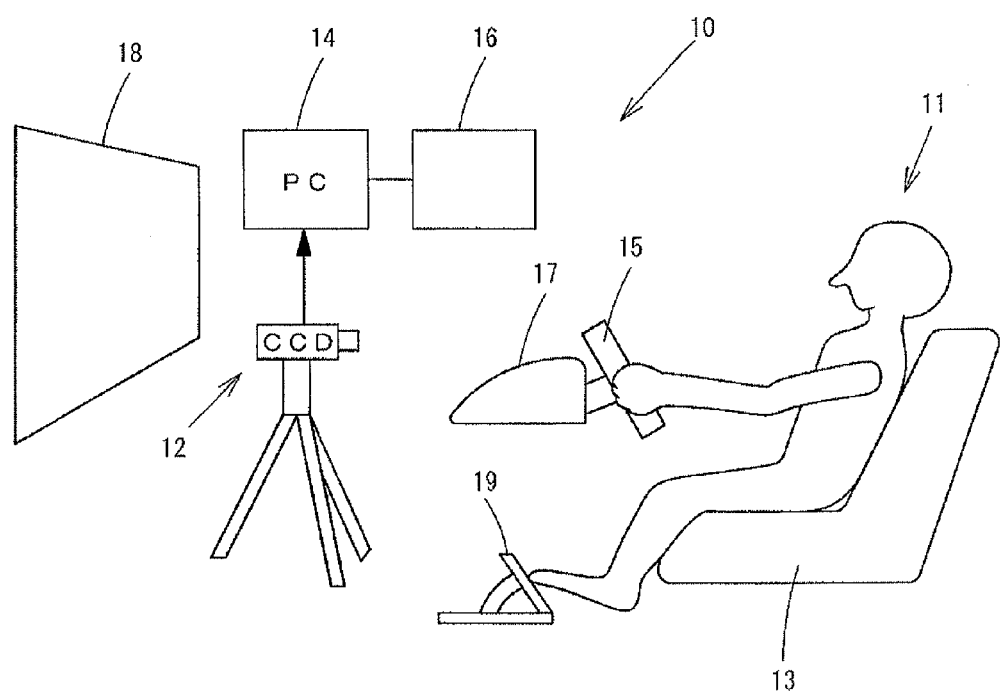
FIG. 8 is a schematic view of an experimental system for showing an example in an embodiment of the present invention.

Next, an example according to an experimental system including the configuration of the doze detection apparatus of the present invention will be described. FIG. 8 shows a schematic view of the experimental system including the doze detection apparatus. The experimental system is configured by the photographing unit 12, including a CCD camera and the like, that photographs a face of a subject 11, and a computer 14 in which a doze detection program that performs detection of a blink by processing an image generated by the photographing unit 12, and the like is installed. The computer 14 is connected to the monitor 16, such as a liquid crystal display, that displays a photographed image. Further, a screen 18 displaying a visibility during driving is provided and a sheet seat 13 on which the subject 11 sits, a steering wheel 15, an instrument display unit 17, an accelerator 19, etc. are included. Thus, the experimental system has a similar configuration to a normal automobile. Furthermore, face expression of the subject 11 during the experiment was recorded in order to obtain rated sleepiness which is a relative index indicating an arousal degree of the subject 11 during the experiment. In this case, degrees of sleepiness were evaluated by two examiners for several subjects 11, and rated sleepiness of the subjects 11 was digitized by point rating. Further, an average of determination values by two examiners was set to rated sleepiness, the rated sleepiness was smoothed by 30 seconds moving average by every 5 seconds, and plotted on a graph. The rated sleepiness was digitized by imparting the following values.

5. Quite awake
4. Slightly drowsy
3. Moderately drowsy
2. Significantly drowsy
1. Sleep In the example, the determination reference value $Th_O$ of blink burst defined as the first threshold time was set to 1 second. Firstly, a distribution of first closed eye times (upper level) according to the definition of a blink burst in the present invention, and a distribution of first closed eye times (lower level) according to a conventional definition of a blink burst, for two subjects (Sub. 1-1, Sub. 2-1), are shown in FIG. 9. The vertical axis shows the first closed eye time of blink burst, and the horizontal axis shows the rated sleepiness. FIG. 9 shows when the rated sleepiness is 2 to 3, from comparison between the first closed eye time of blink burst according to the definition of the present invention (FIG. 2(*a*)) and the first closed eye time of blink burst according to the conventional definition of blink (FIG. 2(*b*)), it can be seen that there is a larger number of blink bursts with eye closures equal to or longer than 1 second in the graph according to the definition of the present invention in the upper level. Further, a distribution of second closed eye times (upper level) according to the definition of a blink burst in the present invention, and a distribution of second closed eye times (lower level) according to the conventional definition of a blink burst, for other two subjects (Sub. 8-1, Sub. 6-2), are shown in FIG. 10. The vertical axis shows the second closed eye time of blink burst, and the horizontal axis shows the rated sleepiness. FIG. 10 shows when the rated sleepiness is 2 to 3, from comparison between the second closed eye time of blink burst according to the definition of the present invention (FIG. 2(*a*)) and the second closed eye time of blink burst according to the conventional definition of blink (FIG. 2(*b*)), it can be seen that there is a larger number of blink bursts with eye closures equal to or longer than 1 second in the graph according to the definition of the present invention in the upper level. This is because, it is possible to detect a blink burst including a long eye-closure by the definition of blink burst according to the present invention, since only a time when the eye is open is defined as a blink interval, however, as shown in FIG. 3(*b*), it is not possible to detect a blink burst including a long eye-closure by the conventional definition, since a stage from an eye closure to an eye opening and a stage from an eye opening to an eye closure are included in a blink interval in addition to an open eye time. As a result, it is clear that the doze detection by the definition of blink burst of the present invention has a possibility of being performed more accurately. Thus, in the example, the doze determination reference $Th_{C1}$ defined as the second threshold time was set to 1 second on the basis of the distribution result of the above-described distributions of the first closed eye times and second closed eye times. Further, the third threshold time (doze determination reference $Th_{C2}$) was set to 2 seconds as a closed eye time that was relatively longer than the second threshold time. In the example, the third threshold time (doze determination reference $Th_{C2}$) was used as the doze determination reference of a blink other than a blink burst (isolated blink).

Figure 11:
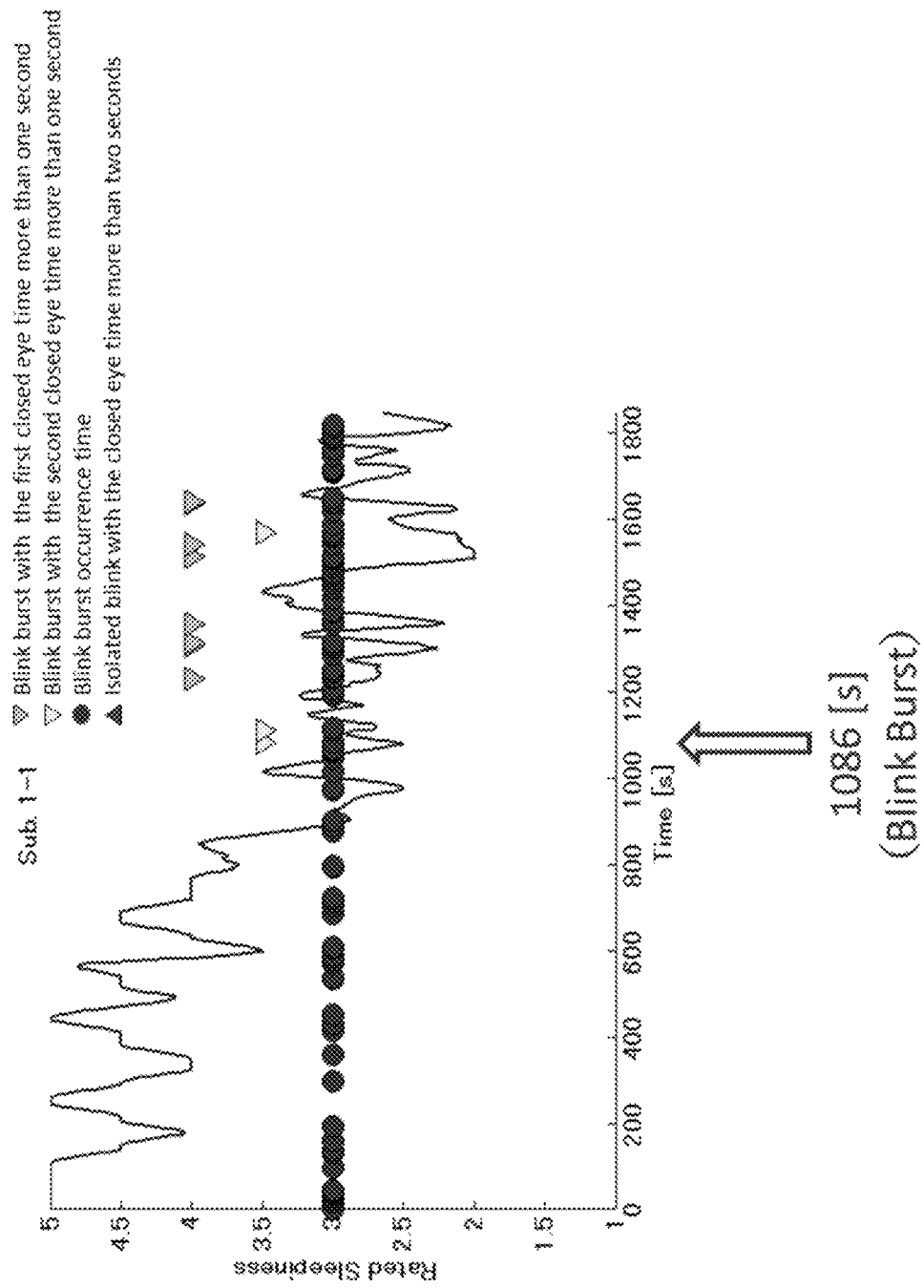
FIG. 11 is a graph showing a doze detection result in an experimental result according to an example of the present invention.

FIG. 11 shows a doze detection by the doze detection method according to the present invention. As shown in FIG. 11, it can be seen that a blink burst of the subject (Sub. 1-1) was detected immediately after starting the experiment (black circle), and then, it was determined to be a doze at a first time point (1086 seconds) where a second eye closure (white triangle facing downward) for 1 second or more was firstly detected. In this time, the rated sleepiness of the subject was varying in up and down direction centering 3, and thus, it can be seen that the subject was resisting the sleepiness. Furthermore, then, the rated sleepiness was decreased to 2, and thus, it can be seen that a state before entering a doze state that caused troubles in driving could be detected. Accordingly, it is confirmed that a doze is accurately detected by the detection method of the present invention.

Figure 12:
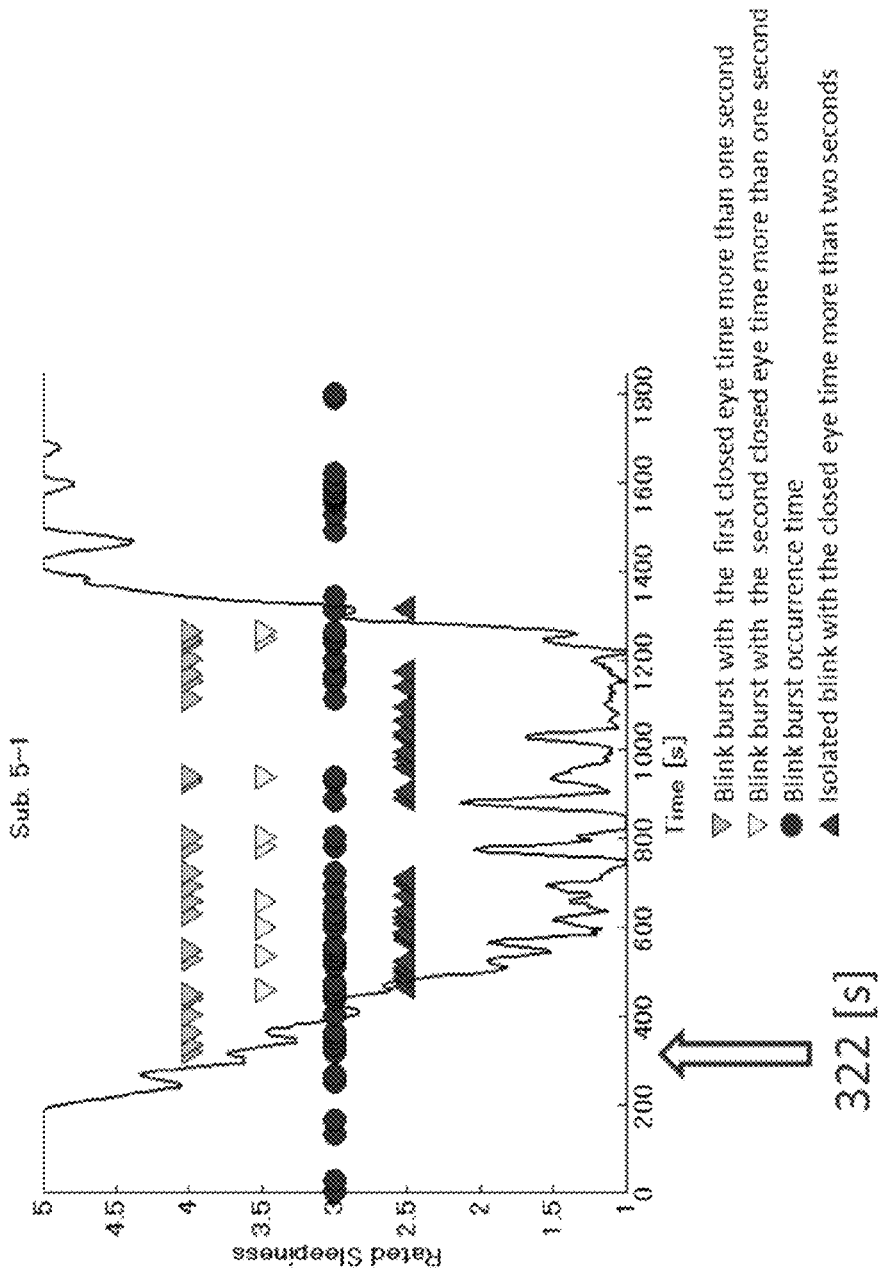
FIG. 12 is a graph showing a doze detection result in an experimental result according to an example of the present invention.

FIG. 12 shows a case related to a subject (Sub. 5-1). Similarly to the subject (Sub. 1-1), a blink burst was detected immediately after starting the experiment (black circle). Then, it was determined to be a doze at a first time point (322 seconds) where a first eye closure (gray triangle facing downward) for 1 second or more was firstly detected. In the state at this time, the rated sleepiness was about 3, and then, the rated sleepiness further decreased. Therefore, it can be seen that the state is in a time when entering a doze state, and thus, it is confirmed that a doze state is accurately detected by the detection method of the present invention.

Figure 13:
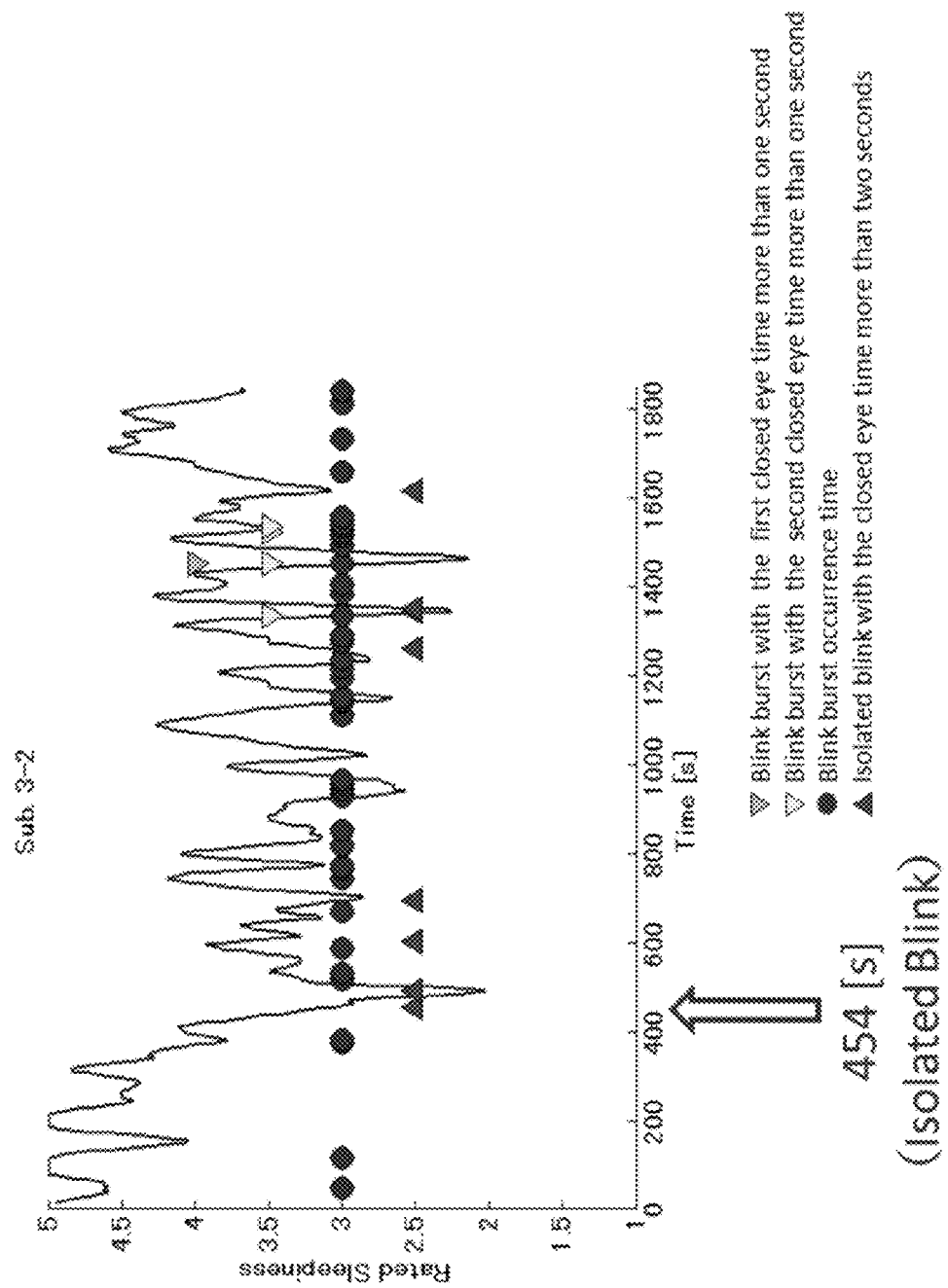
FIG. 13 is a graph showing a doze detection result in an experimental result according to an example of the present invention.

In a case of a subject (Sub. 3-2), that is shown in FIG. 13, a blink burst was detected immediately after starting the experiment (black circle), and it was determined to be a doze at a first time point (454 seconds) where a closed eye time of an isolated blink for 2 seconds or more, that was not a blink burst, was detected (gray triangle facing upward). In the state at this time, the rated sleepiness was about 2, and then, the rated sleepiness varied around 3. Thus, it can be seen that the state is in a time when entering a doze state, and thus, a doze is accurately detected.

Figure 14:
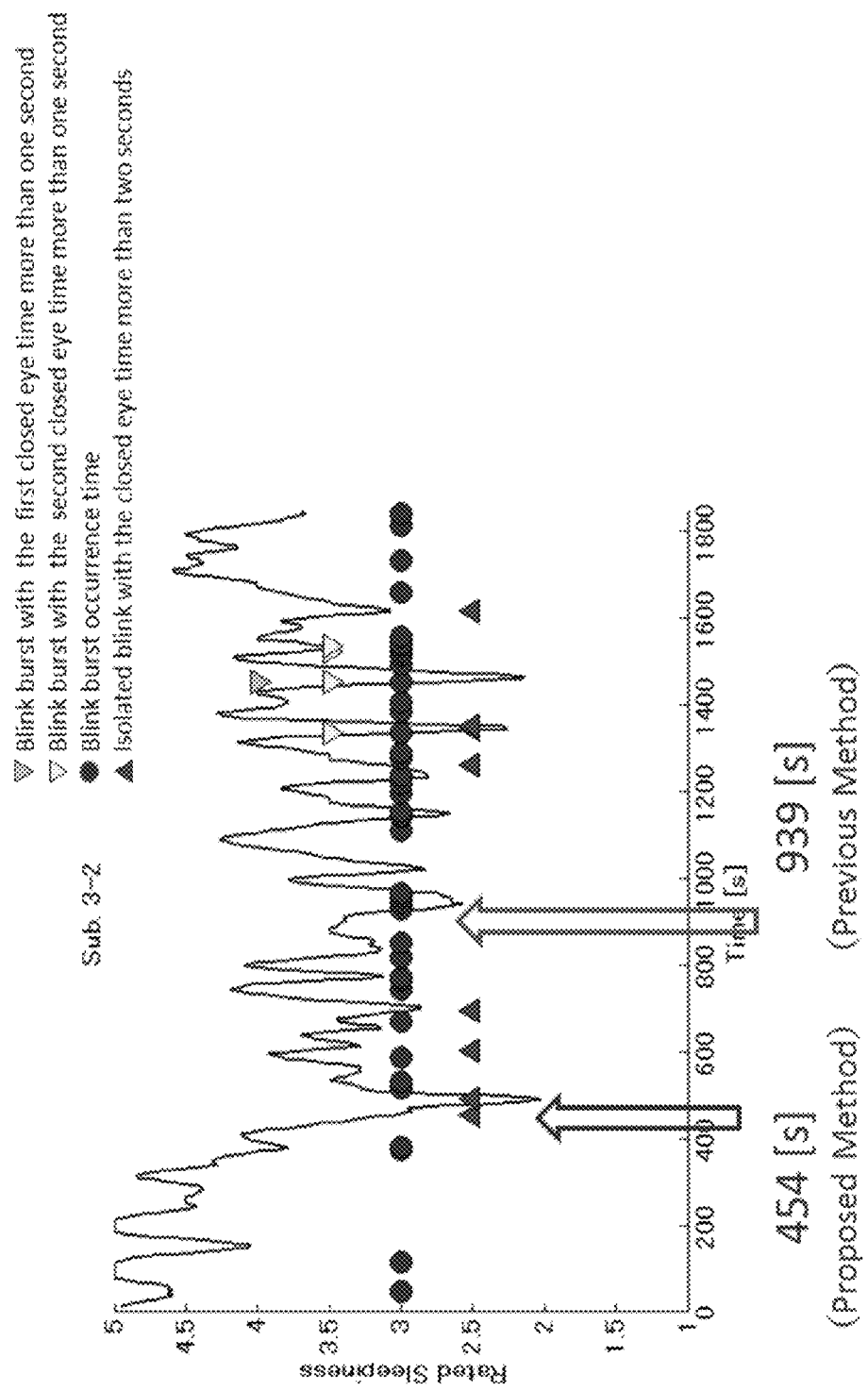
FIG. 14 is a graph showing a time of doze detection according to an example of the present invention and a conventional art.

FIG. 14 shows a difference in doze detection times between the present invention and the previous method, for the subject (Sub. 3-2) of FIG. 13. As the conventional method, the method disclosed in Patent Literature 2 was used. On the basis of the definition of blink burst shown in FIG. 2(*b*), among points where time intervals between a time immediately after a blink burst occurs and an end time of a long eye closure became 10 seconds or less, a time of an earliest point where the time interval became 10 seconds or less was marked. As a result, in the present invention, a doze was detected by determining a closed eye time of an isolated blink for 2 seconds or more (gray triangle facing upward), and thus, a doze could be detected at early timing (454 seconds). In contrast, in the conventional method, the detection timing of the doze is 939 seconds from starting of the measurement, and namely, it is confirmed that the timing is later than that of the method according to the present invention.

Figure 15:
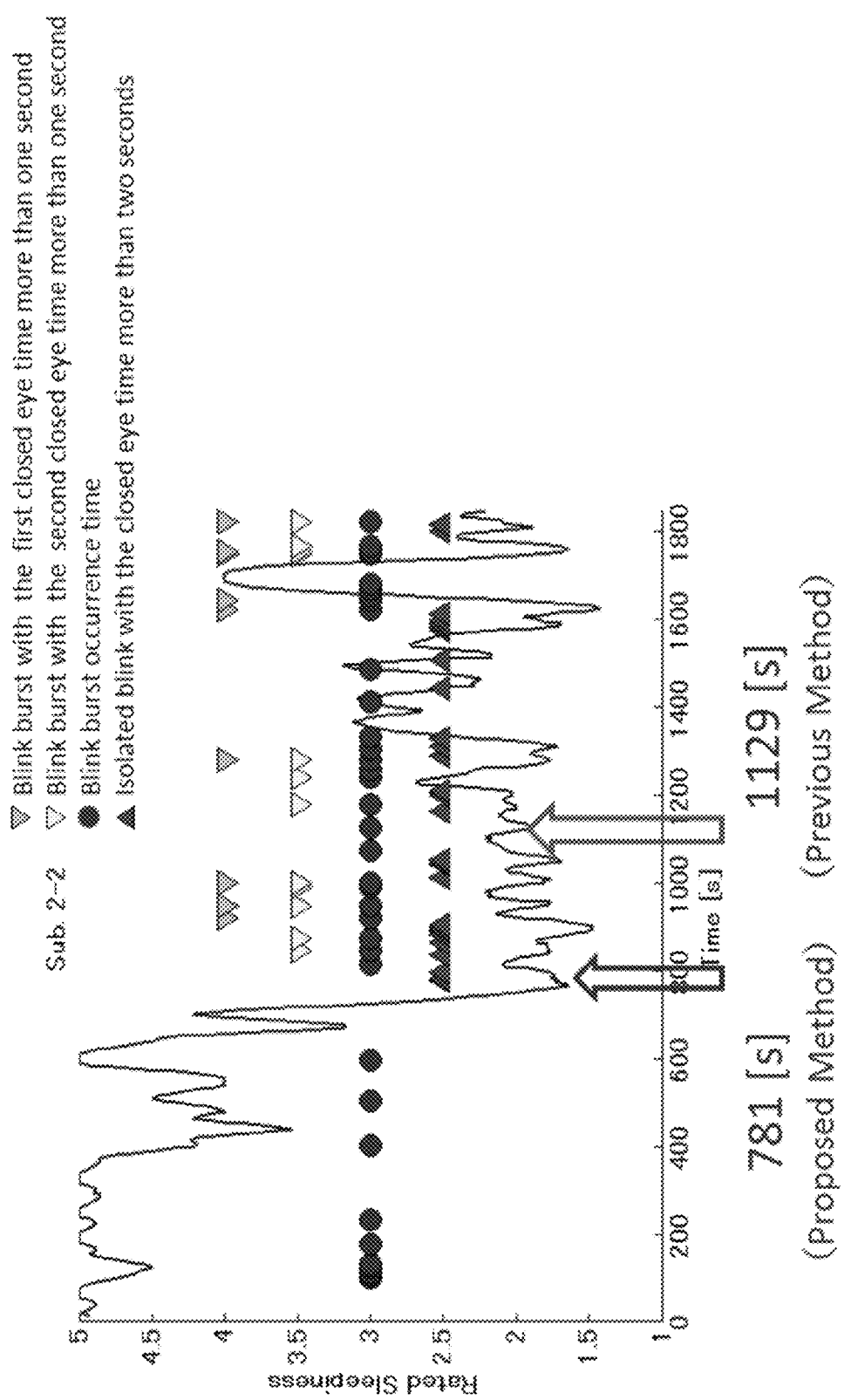
FIG. 15 is a graph showing a time of doze detection according to an example of the present invention and the conventional art.

FIG. 15 shows a result of measuring doze detection times according to the present invention and the previous method, for another subject (Sub. 2-2). In the case of the subject, in the present invention, a doze was detected by determining a closed eye time of an isolated blink for 2 seconds or more (gray triangle facing upward), and thus, a doze could be detected early (781 seconds). In contrast, in the conventional method, the detection timing of the doze is after 1129 seconds from starting of the measurement, and namely, it can be seen that the timing is later than that of the method according to the present invention. Further, as shown in FIG. 15, from a time point where a first eye closure of blink burst for 1 second or more (gray triangle facing downward) is firstly determined and a time point where a second eye closure for 1 second or more (white triangle facing downward) is firstly determined, it can be seen that the detection method of the present invention detects a doze earlier than the conventional method. Accordingly, from this point, it can be seen that the method of the present invention can detect a doze early.

FIG. 16 shows time transition of the rated sleepiness of the subject of FIG. 11 (Sub. 1-1). FIG. 16(a) shows a blink burst occurrence position according to the detection method of the present invention (black circle), and FIG. 16(b) shows a blink burst occurrence position according to the conventional method (white circle). FIG. 16(a) shows a point where the first eye closure (gray triangle facing downward) or second eye closure (white triangle facing downward) during a blink burst for 1 second or more is detected. FIG. 16(b) shows a blink burst occurrence position (white circle) according to the conventional method and a point where a closed eye time of a blink becomes 1 second or more (long eye-closure, gray triangle facing upward).

In the graph of FIG. 16(b) according to the previous method, time points where a long eye-closure after a blink burst is 10 seconds or less are represented by A to E. In the conventional methods, the earliest doze detection timing is 1315 seconds after starting the experiment, that is represented by A. On the other hand, as shown in FIG. 16(a), in the method according to the present invention, a doze is detected at 1086 seconds after starting the experiment, that is a first time point (first white triangle facing downward) where a second eye closure during a blink burst occurs for 1 second or more. Further, in the present invention, from a first time point (first gray triangle facing downward) where a first eye closure during a blink burst occurs for 1 second or more, it can be seen that a doze is detected earlier than the previous method.

Next, an example according to another embodiment with the experimental system (FIG. 8) including the configuration of the doze detection apparatus of the present invention is shown in FIG. 17. FIG. 17 is an experimental result of a subject (Sub. 8-1), FIG. 17(a) shows rated sleepiness, FIG. 17(b) shows a total closed eye time (second) obtained by adding closed eye times of all blinks during a blink burst, FIG. 17(c) shows an average closed eye time (second) of an isolated blink during 30 seconds, and FIG. 17(d) shows time transition of a total closed eye time (second) obtained by adding the closed eye times (second) of all blinks during a blink burst and average closed eye time of an isolated blink during 30 seconds. As a result, it can be seen that the total closed eye time extends in accordance with decrease of the arousal degree. Further, the total closed eye time is always long while the arousal degree decreases. Therefore, it is understood that a doze state is stably detected by measuring the total closed eye time of a blink burst and isolated blink. Further, as shown in Equation (1), when a closed eye time of a j-th blink during a blink burst is $T_B(j)$, and an average closed eye time of an isolated blink is $T_I$, the total closed eye time $T_{sum}$ may be obtained by multiplying these closed eye times by weights ($W_B(j)$, $W_I$) respectively, and by adding the weighted values. In the example shown in FIG. 17, $W_B(j)=1$, and $W_I=1$. However, alternatively, each weight may be variously changed to, for example, $W_B(j)=0.5$ to 1.5, and $W_I=0.5$ to 1.5 and added to obtain the total closed eye time $T_{sum}$.

[Math. 1]

$$T_{sum} = W_1 \cdot T_1 + \sum_j W_B(j) \cdot T_B(j) \quad (1)$$

It is noted that the doze detection apparatus of the present invention is not limited to the above-described embodiments, the blink detection may be performed by other than the above-described method, and it may be determined to be a blink burst when at least two blinks serially occurring in a short time are detected. In addition, the definition and determination reference value of open eye time and closed eye time of the present invention include a numerical value rounded into an integer. Specifically, for example, the definition of 1 second according to the present invention includes a range from 0.5 seconds to less than 1.5 seconds, and the range may be determined as 1 second.

REFERENCE SIGNS LIST 10 doze detection experimental system
11 subject
12, 32 photographing unit
14 personal computer
16 monitor
30 doze detection apparatus
31 driver
33 driver monitor ECU
34 navigation system
35 speaker
36 brake control device

The invention claimed is:

1. A doze detection method comprising:
   measuring an open eye time and a closed eye time of a human eye, the open eye time being a state in which the eye is open among states between an eye closure to an eye opening thereof, and the closed eye time being a state other than the state in which the eye is open;
   setting a first threshold time, the first threshold time being shorter than an average open eye time of a healthy adult in an alert state;
   setting a second threshold time, the second threshold time being longer than an average closed eye time of a healthy adult in an alert state;
   making a first doze state determination in which existence of a doze state is immediately determined when (i) the measured open eye time is determined to be equal to or shorter than the first threshold time and (ii) the measured closed eye time of a blink occurring immediately after the measured open eye time determined to be equal to or shorter than the first threshold time reaches the second threshold time or more;
   setting a third threshold time, the third threshold time being a closed eye time that is longer than the second threshold time; and
   making a second doze state determination to again determine the existence of the doze state when a closed eye time of a blink reaches the third threshold time or more, the blink occurring after an open eye time equal to or shorter than the first threshold time.

2. The doze detection method according to claim 1, further comprising immediately determining the existence of the doze state at an end of a measured open eye time equal to or shorter than the first threshold time, when a closed eye time of a blink occurring immediately before the open eye time equal to or shorter than the first threshold time is determined to be equal to or longer than the second threshold time.

3. A doze detection method comprising:
   measuring an open eye time and a closed eye time of a human eye, the open eye time being a state in which the eye is open among states between an eye closure to an eye opening thereof, and the closed eye time being a state other than the state in which the eye is open;

setting a first threshold time, the first threshold time being shorter than an average open eye time of a healthy adult in an alert state;

setting a second threshold time, the second threshold time being longer than an average closed eye time of a healthy adult in an alert state;

making a first doze state determination in which existence of a doze state is immediately determined when (i) the measured open eye time is determined to be equal to or shorter than the first threshold time and (ii) the measured closed eye time of a blink occurring immediately after the measured open eye time determined to be equal to or shorter than the first threshold time reaches the second threshold time or more;

setting another threshold time, the another threshold time being a closed eye time that is longer than the second threshold time;

in measuring the open eye time, when detecting an eye opening being longer than the first threshold time and an open eye time immediately before occurrence of a blink immediately preceding the eye opening also being longer than the first threshold time, setting the immediately-preceding blink as an isolated blink; and making another doze state determination to immediately determine the existence of the doze state by an end of the eye opening after the isolated blink when a closed eye time of the isolated blink is equal to or longer than the another threshold time.

4. A doze detection method comprising:

measuring an open eye time and a closed eye time of a human eye, the open eye time being a state in which the eye is open among states between an eye closure to an eye opening thereof, and the closed eye time being a state other than the state in which the eye is open;

setting a first threshold time, the first threshold time being shorter than an average open eye time of a healthy adult in an alert state;

setting a second threshold time, the second threshold time being longer than an average closed eye time of a healthy adult in an alert state;

making a first doze state determination in which existence of a doze state is immediately determined when (i) the measured open eye time is determined to be equal to or shorter than the first threshold time and (ii) the measured closed eye time of a blink occurring immediately after the measured open eye time determined to be equal to or shorter than the first threshold time reaches the second threshold time or more;

setting another threshold time, the another threshold time being a closed eye time that is longer than the second threshold time; and making a another doze determination to immediately determine the existence of the doze state, when detecting an eye opening longer than the first threshold time in detecting the open eye time and when a closed eye time of a blink immediately after the eye opening reaches the another threshold time or more.

5. A doze detection apparatus comprising:
a memory; and
a processor configured to execute a program stored in the memory to perform functions comprising:
detecting states from an eye closure to an eye opening of a human eye by recognizing a position of the human eye;
measuring an open eye time and a closed eye time of the human eye, the open eye time being a state in which the eye is open, and the closed eye time being a state other than the state in which the eye is open;

setting (i) a first threshold time which is shorter than an average open eye time of a healthy adult in an alert state, and (ii) a second threshold time which is longer than an average closed eye time of a healthy adult in an alert state;

immediately determine existence of a doze state when (i) the measured open eye time is determined to be equal to or shorter than the first threshold time and (ii) the measured closed eye time of a blink occurring immediately after the measured open eye time determined to be equal to or shorter than the first threshold time reaches the second threshold time or more;

setting a third threshold time as a closed eye time that is longer than the second threshold time; and determining the existence of the doze state when a closed eye time of a blink reaches the third threshold time or more, the blink occurring after an open eye time equal to or shorter than the first threshold time.

6. The doze detection apparatus according to claim 5, wherein the functions performed by the processor further comprise immediately determining the existence of the doze state at an end of the measured open eye time that is determined to be equal to or shorter than the first threshold time, when a closed eye time of a blink occurring immediately before the open eye time equal to or shorter than the first threshold time is determined to be equal to or longer than the second threshold time.

7. A doze detection apparatus comprising:
a memory; and
a processor configured to execute a program stored in the memory to perform functions comprising:
detecting states from an eye closure to an eye opening of a human eye by recognizing a position of the human eye;
measuring an open eye time and a closed eye time of the human eye, the open eye time being a state in which the eye is open, and the closed eye time being a state other than the state in which the eye is open;

setting (i) a first threshold time which is shorter than an average open eye time of a healthy adult in an alert state, and (ii) a second threshold time which is longer than an average closed eye time of a healthy adult in an alert state;

immediately determine existence of a doze state when (i) the measured open eye time is determined to be equal to or shorter than the first threshold time and (ii) the measured closed eye time of a blink occurring immediately after the measured open eye time determined to be equal to or shorter than the first threshold time reaches the second threshold time or more;

setting another threshold time as a closed eye time that is longer than the second threshold time;

when an eye opening that is longer than the first threshold time is detected and an open eye time immediately before occurrence of a blink immediately preceding the eye opening that is also longer than the first threshold time, setting the immediately-preceding blink as an isolated blink; and immediately determining the existence of the doze state by an end of the eye opening after the isolated blink when a closed eye time of the isolated blink is equal to or longer than the another threshold time.

8. A doze detection apparatus comprising:
a memory; and
a processor configured to execute a program stored in the memory to perform functions comprising:

detecting states from an eye closure to an eye opening of a human eye by recognizing a position of the human eye;

measuring an open eye time and a closed eye time of the human eye, the open eye time being a state in which the eye is open, and the closed eye time being a state other than the state in which the eye is open;

setting (i) a first threshold time which is shorter than an average open eye time of a healthy adult in an alert state, and (ii) a second threshold time which is longer than an average closed eye time of a healthy adult in an alert state;

immediately determine existence of a doze state when (i) the measured open eye time is determined to be equal to or shorter than the first threshold time and (ii) the measured closed eye time of a blink occurring immediately after the measured open eye time determined to be equal to or shorter than the first threshold time reaches the second threshold time or more;

setting another threshold time as a closed eye time that is longer than the second threshold time; and immediately determining the existence of the doze state, when an eye opening longer than the first threshold time is measured and when a closed eye time of a blink immediately after the eye opening reaches the another threshold time or more.

9. The doze detection apparatus according to claim 5, wherein the functions performed by the processor further comprise performing control to issue a doze alert when the existence of the doze state is determined.

10. A vehicle comprising the doze detection apparatus according to claim 5.

11. The doze detection apparatus according to claim 5, wherein detecting the states from the eye closure to the eye opening of the human eye includes measuring respective areas of the iris and pupil of the human eye.

* * * * *